United States Patent
Treu

(10) Patent No.: US 7,771,379 B2
(45) Date of Patent: Aug. 10, 2010

(54) FUNCTIONAL ISOLATION OF UPGRADEABLE COMPONENTS TO REDUCE RISK IN MEDICAL TREATMENT DEVICES

(75) Inventor: Dennis M. Treu, Bedford, NH (US)

(73) Assignee: NxStage Medical, Inc., Lawrence, MA (US)

( * ) Notice: Subject to any disclaimer, the term of this patent is extended or adjusted under 35 U.S.C. 154(b) by 621 days.

(21) Appl. No.: 10/699,921

(22) Filed: Nov. 3, 2003

(65) Prior Publication Data

US 2004/0249330 A1 Dec. 9, 2004

Related U.S. Application Data

(60) Provisional application No. 60/423,318, filed on Nov. 1, 2002.

(51) Int. Cl.
*A61M 37/00* (2006.01)
*A61F 5/24* (2006.01)

(52) U.S. Cl. .................... 604/4.01; 128/903

(58) Field of Classification Search .............. 604/8–10, 604/4.01–6.16, 66, 67; 600/300, 573; 607/66–75; 128/897, 903–905, 200.14–200.22
See application file for complete search history.

(56) References Cited

U.S. PATENT DOCUMENTS

| | | | | |
|---|---|---|---|---|
| 4,216,462 A * | 8/1980 | McGrath et al. | ............ | 600/301 |
| 4,808,167 A * | 2/1989 | Mann et al. | ................. | 604/151 |
| 5,401,394 A * | 3/1995 | Markham | .................... | 210/85 |
| 5,417,222 A * | 5/1995 | Dempsey et al. | ............ | 600/509 |
| 5,469,859 A * | 11/1995 | Tsoglin et al. | .............. | 600/536 |
| 6,113,554 A * | 9/2000 | Gilcher et al. | .............. | 600/573 |
| 6,582,387 B2 * | 6/2003 | Derek et al. | ............... | 604/6.14 |
| 6,622,542 B2 * | 9/2003 | Derek et al. | ............... | 73/19.03 |
| 6,641,533 B2 * | 11/2003 | Causey et al. | ............... | 600/300 |
| 6,827,698 B1 * | 12/2004 | Kleinekofort | .............. | 604/6.06 |
| 2001/0034614 A1 * | 10/2001 | Fletcher-Haynes et al. | ..... | 705/2 |

\* cited by examiner

*Primary Examiner*—Leslie R Deak
*Assistant Examiner*—Philip R Wiest
(74) *Attorney, Agent, or Firm*—Miles & Stockbridge P.C.; Mark A. Catan

(57) ABSTRACT

A medical treatment system isolates more risk-sensitive equipment from less risk-sensitive components of a treatment device to allow upgrades to be made to the latter more easily without an concomitant increase in risk to a patient caused by upgrades. For example, the latter may serve a pure monitoring function while the former encapsulates the treatment functions thereby preventing errors from the latter from propagating into the treatment-sensitive portions of the device.

37 Claims, 3 Drawing Sheets

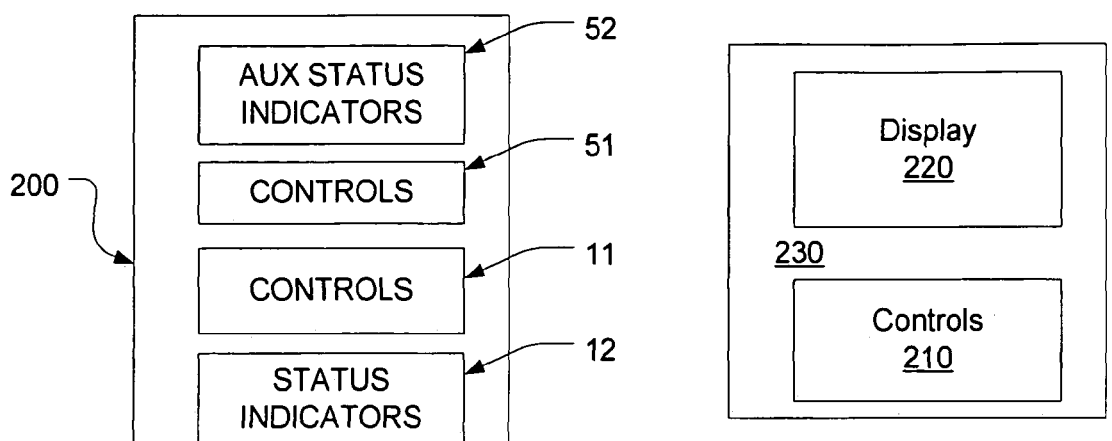
FIG. 2
FIG. 3
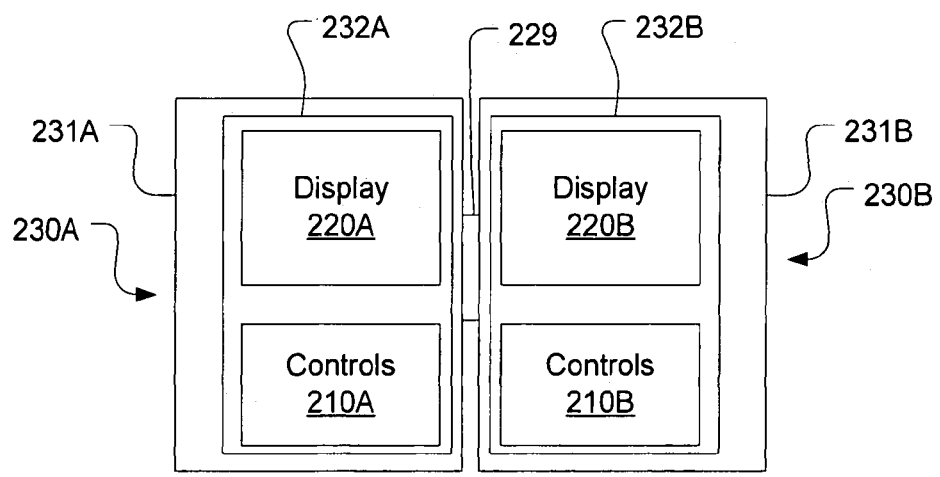
FIG. 4

FUNCTIONAL ISOLATION OF UPGRADEABLE COMPONENTS TO REDUCE RISK IN MEDICAL TREATMENT DEVICES

CROSS REFERENCE TO RELATED APPLICATIONS

The present application claims priority to U.S. Patent Application Ser. No. 60/423,318, filed Nov. 1, 2002, which application is hereby incorporated by reference as if fully set forth in its entirety herein. The present application also claims priority to U.S. patent application Ser. No. 09/865,905, filed May 24, 2001, which application is hereby incorporated by reference as if fully set forth in its entirety herein.

BACKGROUND OF THE INVENTION

Medical devices are instrumental in saving or prolonging countless lives. Examples of medical devices include dialysis machines, heart lung machines, respirators, electrocardiogram machines, defibrillators, and pacemakers. Because human lives are at stake, it is of critical importance to avoid malfunctions in such medical devices. Many medical treatment systems may benefit from frequent upgrades of their capabilities, but such upgrades can run the risk of modifying the behavior of treatment systems in unexpected ways, creating risk. For example, many sophisticated treatment devices such renal replacement therapy machines employ software in their control and performance monitoring mechanisms. Software is easily modified, but can profoundly impact safety. In its General Principles of Software Validation; Final Guidance for Industry and FDA Staff Document issued on: Jan. 11, 2002, the Food and Drug Administration (FDA) reported its analysis of 3140 medical device recalls conducted between 1992 and 1998, which revealed 7.7% were attributable to software failures. Of those software related recalls, 79% were caused by software defects that were introduced when changes were made to the software after its initial production and distribution.

In addition to the risk, government regulation of medical devices make upgrades expensive for manufacturers and vendors and impose delays in the introduction of improved systems. To protect the public from failures caused by system upgrades, governments often regulate the sale and use of medical devices and require additional testing and proof of safety every time a treatment device is modified. When a manufacturer wishes to release an improved version of a device, the manufacturer must go through expensive, and time-consuming regulatory approval process to establish the efficacy and safety of the improvements. Because of this, many patients are deprived from the benefits that recent advances in medical technology might otherwise provide. In regimes where such testing is not onerous, the risk is still present.

SUMMARY OF THE INVENTION

Instead of designing a medical device that must be upgraded in order to add improvements, the inventors have recognized that upgradeability can be obtained by separating portions of a medical treatment device with differing tendencies to impact safety or performance so as to isolate the risks of making upgrades. For example, a machine may be divided by a first component that includes critical treatment actuators and sensors and which is operable as a stand-alone device and a second component that includes data logging, data reduction, display, and various non-critical annunciator functions. These may be termed a treatment device and an auxiliary status-reporting device (ASRD), for convenience. In such a system, the two may be mechanically separated such that the medical device transmits information to the ASRD by a one-way communications channel to ensure that there is no way for the latter to affect the state of the former. In such an embodiment, this information would let the ASRD know what is going on inside the medical device. The ASRD may manipulate this information and report the status of the medical device to an operator. In this example, notably, the ASRD does not control the medical device. Control of the medical device can only be accomplished by manipulating the controls on the medical device itself.

Preferably, the transfer of information occurs in one direction only—from the medical device to the ASRD. It is possible to exchange information if care is taken to ensure that an error condition in the ASRD cannot propagate into an error condition in the medical device. Alternatively, layers of operation may be defined to ensure that errors cannot propagate into critical subsystems. In a preferred embodiment, no information flows back from the ASRD to the medical device. In this case, it becomes impossible for the ASRD to affect the operation of the medical device. With this arrangement, upgrades to the ASRD can be made without the risk of adversely affecting the treatment delivered by the medical device. Also, only the medical device itself may be required to undergo the rigorous regulatory approval process to establish efficacy and safety whenever an upgrade is made.

The functions of the medical device and ASRD may be divided such that an operator may use the ASRD to figure out what is happening in the medical device and to monitor the progress of the medical procedure for which the medical device is being used. In order to modify the medical procedure being administered based on information obtained from the ASRD, the operator must adjust the controls of the medical device itself. Preferably, the medical device itself includes its own set of status indicators. Before adjusting the controls of the medical device, the operator can verify the state of these status indicators. These status indicators provide an additional level of safety, and reduce the chance that a medical procedure will be administered in an improper manner.

The requirement of an intervening operator is not the only dividing line between operations of the medical device and ASRD that may be employed. There is a risk that an ASRD that gives instructions for changing the settings of the medical device can cause errors to propagate into a treatment operation by way of an operator. Thus, the ASRD may be "isolated" using a more rigorous standard. The ASRD functions may defined as ones that are purely for relating non-critical system parameters that may not be used by an operator to make changes in the medical device's system settings. For example, the outputs of the ASRD may be restricted to non real-time output.

BRIEF DESCRIPTION OF THE DRAWINGS

FIG. 2 is block diagram of a control panel in which different types of controls and annunciator devices, which are isolated, are combined together to form a single control panel, but which are grouped separately.

FIG. 3 is a block diagram of a control panel in which different types of controls and annunciator devices, which are functionally isolated but otherwise integrated into a single control panel.

FIG. 4 is a block diagram of separate control panels, one for a treatment machine and one for an auxiliary monitoring device which are separately housed but which can be placed side-by-side for operational convenience.

DETAILED DESCRIPTION OF THE PREFERRED EMBODIMENTS

Figure 1:
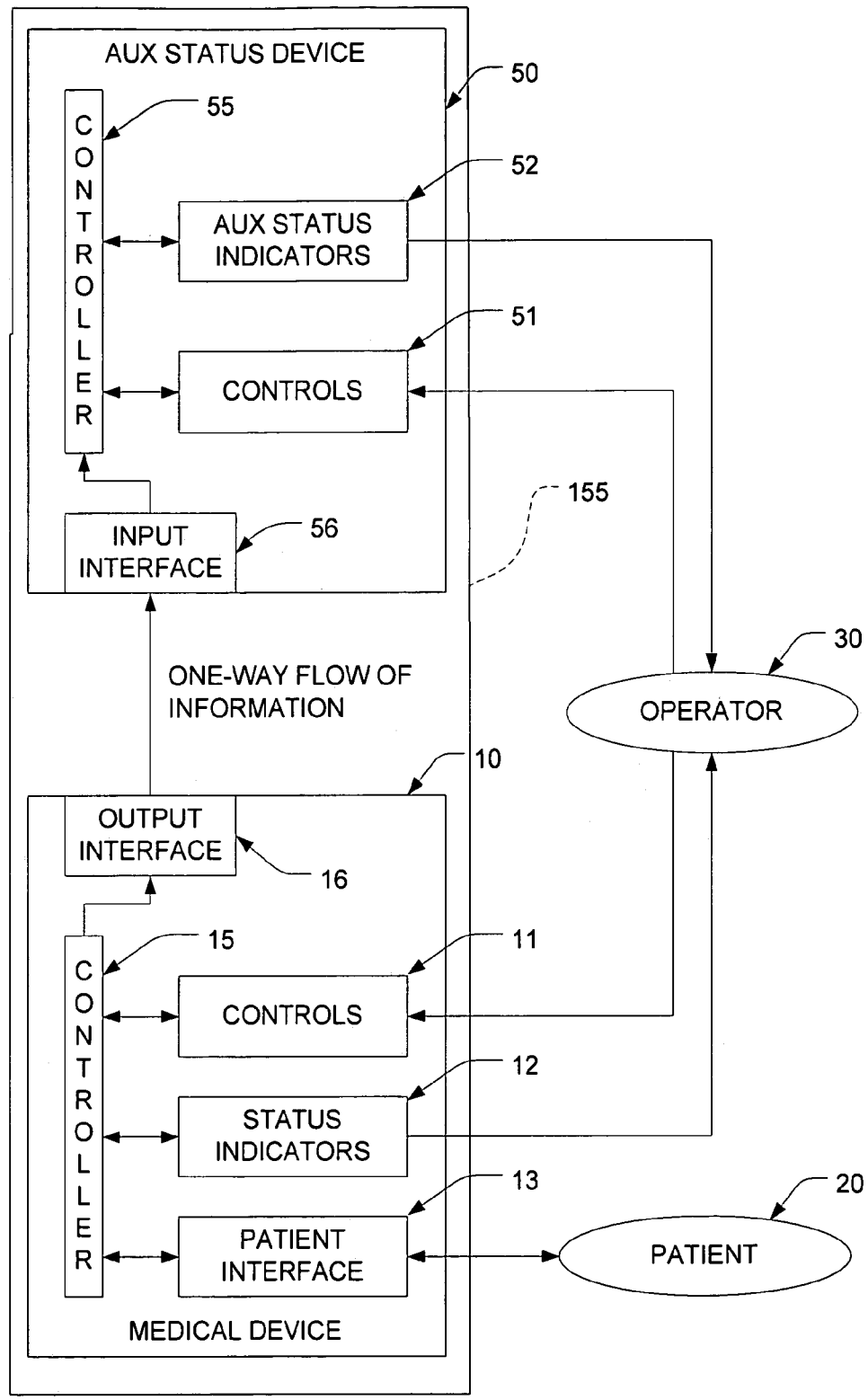
FIG. 1 is a block diagram of a system that includes a medical device and an auxiliary status reporting device.

FIG. 1 depicts a system that includes a medical device 10 and an auxiliary status-reporting device (ASRD) 50. The medical device includes a set of controls 11 which are preferably implemented on a suitable control panel. These controls can be manipulated by the operator 30 in order to control the operation of the medical device 10. The medical device 10 also includes a set of status indicators 12 that provide feedback to the operator 30, and a patient interface subsystem 13. This subsystem 13 interfaces with the patient 20 in a manner that will depend on the medical procedure for which the medical device 10 was designed. For example, if the medical device 10 is a dialysis machine, the patient interface 13 may include appropriate components to receive blood from the patient, process the blood, and return the blood to the patient 20.

A controller 15 interacts with the controls 11, the status indicators 12, and the patient interface subsystem 13 in to ensure that the medical device 10 performs its intended function. The design of the controls 11, status indicators 12, patient interface subsystem 13 and the controller 15 may be in accord with the designs of various conventional medical devices known to persons skilled in the relevant art. Accordingly, details of the operation of the medical device 10 are not discussed herein. A distinction between the medical device 10 of the present invention and conventional medical devices is that the controller 15 is configured to output information that describes the status of the medical device 10 in detail. Preferably, the output information is extensive (or as close to exhaustive as possible) such that features may be added to the ASRD 50 without being hindered by insufficient information. This information is output to the world outside of the medical device 10 via the output interface 16. The ASRD 50 and medical device 10 may be co-located or even housed in a common housing 155.

It will usually be necessary to modify the components 11-15 (as compared to their conventional designs) so that complete information about the medical device 10 can be transmitted. For example, sensors ordinarily configured to provide status information directly to an observer may preferably include the ability to transmit multiplex information onto a data channel. Examples of status indicators 12 include lamps, LEDs, dials, rotating pointers, etc. Suitable modifications (e.g. adding buffers and data busses, optical rotation sensors, multiplexers, etc.) may be required to enable these status indicators 12 to report their status to the controller 15. Once the controller 15 obtains this status information, the controller 15 can report it via the output interface 16.

Examples of controls 11 include knobs, dials, and switches. These controls may also require modification so that the state of all of the controls on the medical device 10 can be ascertained by the controller 15. For example, if one of the controls was a dial that controls the speed on a pump, the position of that dial can be sensed using any conventional approach (e.g., an optical sensor or a potentiometer). Once the controller 15 ascertains the status of all the controls, the controller 15 can report that information via the output interface 16.

Examples of the patient interface subsystem 13 include blood filters, high-voltage generators, and electrical impulse generators. These subsystems 13 may also require modifications so that complete information about the operation of the medical device 10 can be provided to the outside world.

Communication between the various subsystems 11-15 of the medical device 10 may be implemented using analog and/or digital electronics, in any conventional manner.

When the medical device 10 is being used to treat the patient 20, the operator 30 will control the medical device 10 via the controls 11, and monitor the status of the treatment via the status indicators 12. While treatment is being monitored in this manner by the operator 30, information about the status of the treatment and the medical device 10 is being transmitted out of the medical device 10 via the output interface 16.

The ASRD 50 has an input interface 56 that is designed to receive information that comes out of the medical device 10 via the output interface 16. The controller 55 accepts the information that arrives at the ASRD 50 via the input interface 56. The controller 55 is preferably implemented using a microcontroller or a microprocessor, but may also be implemented using discrete electronic components.

The controller 55 processes the information received via the input interface 56. Based on this information, the controller 55 can discern what is happening in the medical device 10. The controller 55 takes this information and analyzes it. The results of the analysis of this information are then reported to the operator 30 using the auxiliary status indicators 52. The auxiliary status indicators 52 are used to inform the operator 50 of the events that are occurring in the medical device 10. Examples of suitable hardware that can be used to serve as the auxiliary status indicators 52 include lamps, LEDs, rotating pointers, bar graphs, CRTs, and flat panel displays. Audio, vibration, radio, and other output devices may be employed as well. For example, stored speech commands may be output in response to an emergency situation guiding the operator or patient to take compensatory actions.

The controls 51 are used to accept commands from the operator 30. The operator 30 can select which information should be provided to him or her (via the status indicators 52) by operating the controls 51. In some embodiments, the operator can also select the format in which the information will be provided (e.g. bar graphs, line graphs, numeric displays, etc.) by operating the controls 51. The controller 55 recognizes when the controls 51 are being operated, and responds accordingly.

For example, if the medical device 10 is a dialysis machine, the patient interface subsystem 13 might measure the blood pressure of the patient, the blood temperature, the red blood cell count of the patient, the volume of blood removed from the patient, and the volume of fluid returned to the patient. The controller 55 could be configured to display a history of the patient's blood pressure in response to a first command from the operator 30 received via the controls 51, and it could be programmed to display a history of the blood temperature in a graphical format based on the receipt of a second command from the operator 30 via the controls 51. Since the controller 55 has received information describing all the events occurring in the medical device 10 since the start of the procedure, the controller can provide the operator 30 with the desired information via the auxiliary status indicators 52.

In one preferred embodiment, the auxiliary status device 50 is implemented in a computer running a standard operating system, such as Windows, Linux, or Unix. In such a case, the controls 51 might be a conventional keyboard and mouse, while the status indicators 52 could be a conventional CRT or flat-panel display. Conventional touch screens may also be used as a combination control/status indicator device. The interplay between the operator 30 and ASRD 50 may be implemented using any of a variety of well-known techniques for interfacing a computer with an operator.

Optionally, the ASRD 50 may be configured to communicate with a remote device (e.g., via the internet, an extranet, a local area network, etc.). When such a connection to a remote device is used, the remote device may be configured to access all of the information that was transmitted from the medical device 10 to the ASRD 50, and use that information for any desired purpose. The remote device can also be used to control the ASRD and even to upgrade the software that is being run on the ASRD 50.

Transfer of information from the medical device 10 to the ASRD 50 may be implemented using any conventional communication technique. Examples of suitable communication protocols include IRDA and Bluetooth.

Preferably, the output interface 16 of the medical device 10 is configured so that no information from the ASRD can affect the operation of the medical device 10 (except indirectly by manual actuation of the controls 11 on the medical device 10 itself). This may be accomplished, for example, by using a transmit-only interface device (e.g., an optical emitter or a radio frequency transmitter) in the medical device 10 without including a corresponding receiver. Another example is simply using opto-isolators in a wired communication channel.

According to an embodiment, a single control panel 200 integrates status indicators 12, auxiliary status indicators 52, control 11 and controls 51.

FIG. 2 is block diagram of a control panel in which different types of controls and annunciator devices, which are isolated, are combined together to form a single control panel, but which are grouped separately. The embodiment of FIG. 1 suggests that auxiliary status indicators 52, controls 51, status indicators 12 and controls 11 are housed in separate unitary devices, namely medical device 10 and ASRD 50. The functional isolation may be accomplished, however, by incorporating the functions of the auxiliary status indicators 52, controls 51, status indicators 12 and controls 11 into a single control panel or interface 200 as indicated in FIG. 2. These may be grouped separately in a single control panel as illustrated in FIG. 2, or they may be interspersed as illustrated in FIG. 3. FIG. 3 is a block diagram of a control panel 230 in which different types of controls and annunciator devices including display 220 and control 210 components are functionally isolated but otherwise integrated into a single control panel 230.

FIG. 4 is a block diagram of separate control panels 232A and 232B, one for a treatment machine 230A and one for a ASRD 230B. Each control panel as a respective one or more displays 220A/220B and a respective one or more controls 210A/210B. Each also has a separate respective housing, a first housing 231A for the treatment device 230A and a second housing 2303 for the ASRD 230B. The treatment machine 230A and the ASRD 230B may be configured as separate unitary devices which may be located side-by-side connected by a communications interface 229.

Figure 5:
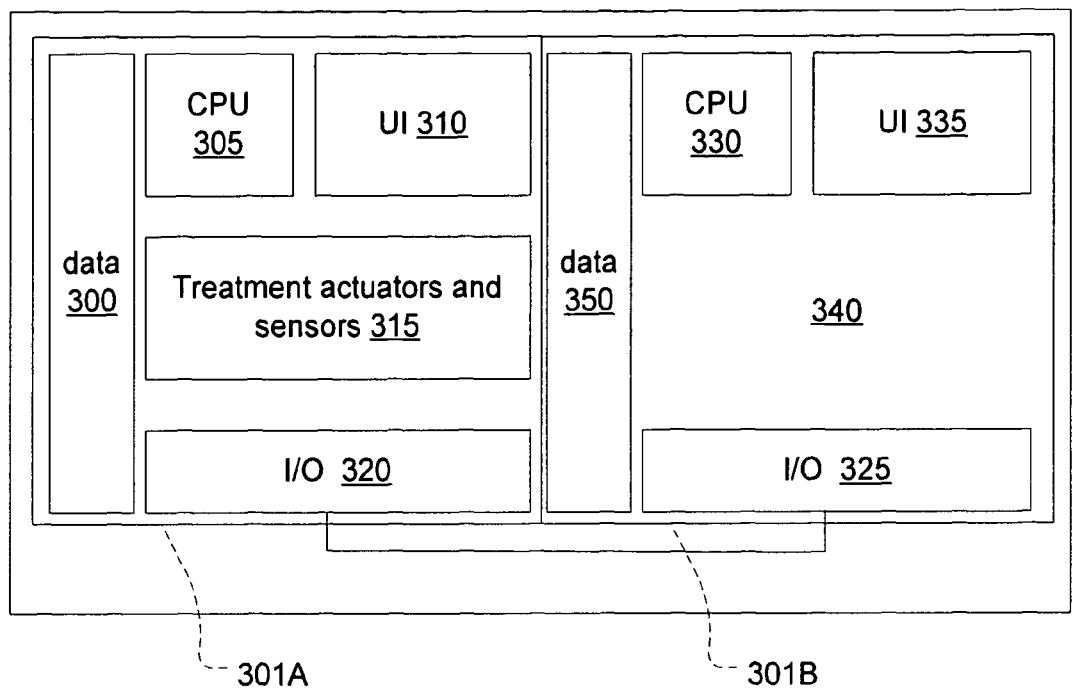
FIG. 5 is an illustration of a unitary treatment and monitoring device with separate control systems for treatment and pure monitoring functions illustrated by way of a digital control scheme.

FIG. 5 is an illustration of a unitary treatment and monitoring device 340 with separate control systems 301A and 301B for treatment (301A) and monitoring (301B) functions. The treatment control system 301A includes a programmable processor 305 that runs software stored in memory 300 controlling output and responding to inputs through a user interface 310. The treatment control system 301A processor 305 also controls treatment actuators and sensors 315. The monitoring control system 301B includes a programmable processor 3330 that runs software stored in memory 350 controlling output and responding to inputs through a user interface 335. Respective I/O interfaces, one 320 for the treatment control system 301A and one 325 for the monitoring system are linked to convey information between the two.

The functions performed by the monitoring system 301B may enhance functions already performed by the treatment system 301A. The latter may already output sensor data or error conditions in a certain format. However, the same data may be output in an enhanced format by the monitoring system 301B. For example, the treatment system 301A may output instantaneous pressure of a portion of a blood circuit in a numerical display forming part of the user interface 310. The monitoring system 301B may enhance this data by storing a time-series of pressure signals and displaying through user interface 335 a time-graph of the time series of pressure signals. Another example is where the monitoring system 301B outputs a graphical representation of the instantaneous pressure signal with high and low limits indicated as a bar graph (not illustrated) with upper and lower bounds represented as lines to give a more easily understood representation of the current pressure signal. Another example is that the monitoring system 301B may be employed to translate cryptic error codes into verbose format with instructions for trouble-shooting. Yet another example is during set-up of the system, an online user manual stored in memory 350 may be output by the user interface 335 and controlled according to signals from the treatment system 301A. Yet another example is that the monitoring system 301B may translate the language of data from the treatment system 301A.

Figure 6:
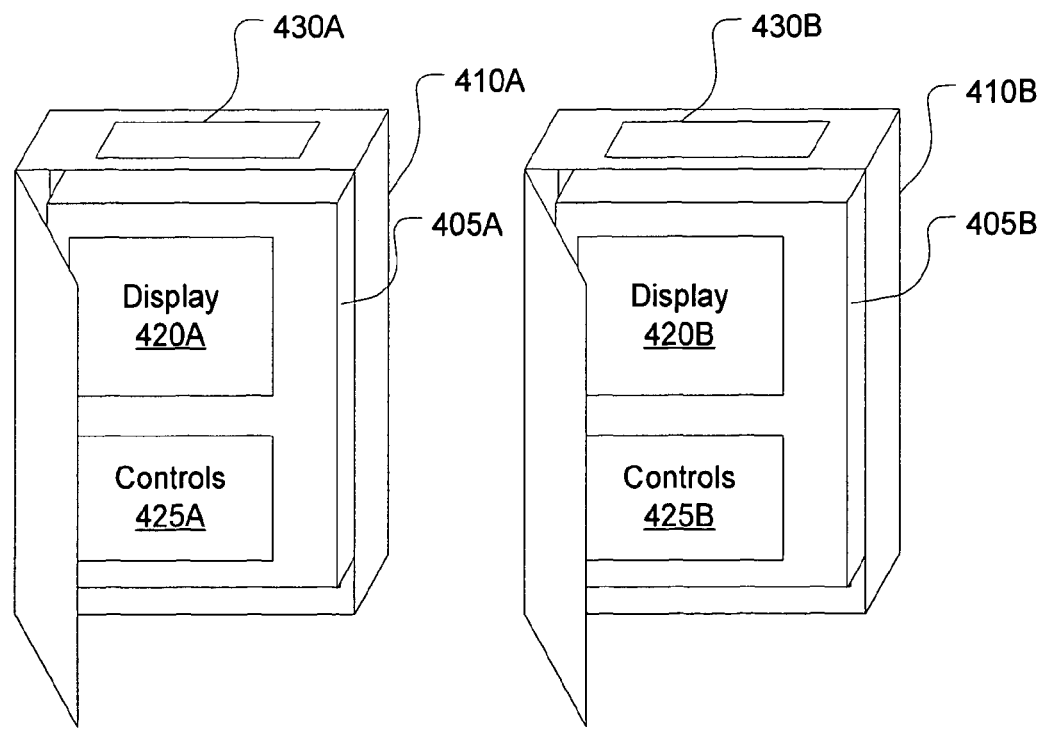
FIG. 6 is an illustration of separate devices that encapsulate respective treatment-critical and treatment non-critical functions in separate housings and which are packaged and labeled separately.

FIG. 6 is an illustration of separate devices treatment 405A and monitoring 405B devices that encapsulate respective treatment-critical and treatment non-critical functions in separate housings. They are packaged in separate containers 410A and 410B with separate labels 430A and 430B to give an indication to users that one is a monitoring only device and one is a medical treatment device which may be treated differently by, for example, a hospital's regulations.

The invention claimed is:

1. A medical treatment device comprising:
    a single treatment unit configured to administer a medical treatment to a patient, the treatment unit including user-accessible controls configured to permit control of the administration of the medical treatment and indicators configured to show status information relating to the medical treatment, the treatment unit having a programmable processor;
    a programmable monitor unit with at least one display and at least one control configured to permit the selection of information to be shown on the display, the programmable monitor unit further having a memory for storing executable instructions thereon; the monitor unit being configured to process treatment data from the treatment unit responsively to the executable instructions stored in its memory,
    the monitor unit being positioned adjacent the treatment unit such that a single user has simultaneous physical access to the treatment unit controls and indicators and the monitor unit controls and display; and
    a one-way communication mechanism operatively connecting the treatment unit to the monitor unit such that the monitor unit is prevented from sending signals to the treatment unit at all times during operation of the medical treatment device and such that the monitor unit receives data from the treatment unit, the monitor unit being configured to output at least data relating to a status of the medical treatment being administered by the treatment unit;

the monitor unit being configured to receive changes to instructions stored in the memory from a remote device by which the monitor unit's function is modified;

the monitor unit being configured to process the treatment data from the single treatment unit, exclusively.

2. The device of claim 1, wherein the treatment unit and the monitor unit are connected to a common control panel with inputs and outputs, each connected such that any signals from the monitor unit are prevented from being transmitted to the treatment unit.

3. The device of claim 2, wherein the treatment unit, the monitor unit, and the control panel are located within a common housing.

4. The device of claim 1, wherein the monitor unit is configured to output on the display at least one of a time-series of sensor signals received over the one-way communication mechanism, a graphical representation of sensor signals received over the one-way communication mechanism, maximum and minimum sensor signal values received over the one-way communication mechanism, text adding information to information received over the one-way communication mechanism, and troubleshooting information responsive to information received over the one-way communication mechanism.

5. The device of claim 1, wherein signals from the monitor unit are physically prevented from being transmitted to the treatment unit.

6. The device of claim 1, wherein the one-way communication mechanism lacks the ability to transmit signals to the treatment unit.

7. The device of claim 1, wherein the monitor unit and treatment unit are configured to be located adjacent the patient being treated.

8. The device of claim 1, wherein the monitor unit at least one control includes multiple controls and the display includes a graphical display.

9. The device of claim 1, wherein the one-way communication mechanism is an opto-isolator that only permits signals to be transmitted from the treatment unit to the monitor unit.

10. The device of claim 1, wherein the monitor unit is further configured to transfer treatment information to a remote device.

11. The device of claim 10, wherein the monitor unit is further configured to permit it to be controlled by the remote device.

12. A medical treatment device comprising:

a treatment unit configured to administer a medical treatment to a patient, the treatment unit including user-accessible controls configured to permit the control of the administration of the medical treatment and indicators configured to show status information relating to the medical treatment, the treatment unit having a memory and a programmable processor configured to execute software instructions stored in the memory;

a programmable monitor unit with at least one display and at least one control configured to permit the selection of information to be shown on the display, the programmable monitor unit further having a memory for storing executable instructions thereon; the monitor unit being configured to process treatment data from the treatment unit responsively to the executable instructions stored in its memory; and a one-way communication mechanism configured to provide a dedicated connection for transmitting treatment data from the treatment unit to the monitor unit such that signals from the treatment unit are received by the monitor unit but such that signals from the monitor unit are permanently prevented from being received by the treatment unit, the monitor unit being dedicated exclusively to the treatment unit such that it receives treatment data exclusively from the treatment unit;

the monitor unit being configured to receive changes to instructions stored in the memory by a remote device by which the monitor unit's function is modified;

the treatment unit outputting at least data relating to a status of the medical treatment administered by the treatment unit.

13. The device of claim 12, wherein the treatment unit and the monitor unit are connected to a common control panel with inputs and outputs, each connected such that any signals from the monitor unit are prevented from being transmitted to the treatment unit.

14. The device of claim 12, wherein the monitor unit is configured to output on the display at least one of a time-series of sensor signals received over the one-way communication mechanism, a graphical representation of sensor signals received over the one-way communication mechanism, maximum and minimum sensor signal values received over the one-way communication mechanism, text adding information to information received over the one-way communication mechanism, and troubleshooting information responsive to information received over the one-way communication mechanism.

15. The device of claim 12, wherein signals from the monitor unit are physically prevented from being transmitted to the treatment unit.

16. The device of claim 12, wherein the one-way communication mechanism lacks the ability to transmit signals to the treatment unit.

17. The device of claim 12, wherein the monitor unit and treatment unit are configured to be located adjacent the patient being treated.

18. The device of claim 12, wherein the one-way communication mechanism is an opto-isolator which only permits signals to be transmitted from the treatment unit to the monitor unit.

19. The device of claim 12, wherein the monitor unit is further configured to transfer treatment information to a remote device.

20. The device of claim 19, wherein the monitor unit is further configured to permit it to be controlled by the remote device.

21. A medical treatment device comprising:

a single treatment module configured to administer a medical treatment to a patient, the treatment module including at least one user-accessible control which enables control of administration of the medical treatment, the treatment module having a programmable processor configured to execute software instructions stored in a memory, and a dedicated monitoring module having a memory for storing executable instructions thereon; the monitoring module being configured to process treatment data from the treatment unit responsively to the executable instructions stored in its memory and further being configured to receive the treatment data exclusively from the treatment module and to output at least data relating to a status of the medical treatment being administered, the monitoring module being signally connected to the treatment module exclusively so as to enable data transfer from the treatment module to the monitoring module, and the monitoring module being operatively isolated from the treatment module such that signals from the monitoring module are physically prevented from being transmitted to the treatment module; the monitoring module being configured to receive treatment data exclusively from the single treatment module;

the monitoring module being configured to receive changes to instructions stored in the memory by a remote device by which the monitor module's function is modified.

22. The device of claim 21, wherein the monitoring module is signally connected to the treatment module by a communication device configured to permit signals to only travel from the treatment module to the monitoring module at all times.

23. The device of claim 21, wherein the monitoring module is signally connected to the treatment module by an opto-isolator which only permits signals to travel from the treatment module to the monitoring module at all times.

24. The device of claim 21, wherein the treatment module includes a transmit-only device, the monitoring module includes a receiving-only device, and the treatment module is signally connected to the monitoring module by a communication link between the transmit-only device and the receiving-only device.

25. The device of claim 21, wherein the treatment module is incapable of receiving signals from the monitoring module during operation of the medical treatment device.

26. The device of claim 21, wherein the monitoring module is incapable of sending signals to the treatment module during operation of the medical treatment device.

27. The device of claim 21, wherein the treatment module has a transmitter without a corresponding receiver, the monitoring module has a receiver, and the monitoring module is connected to the treatment module by way of a signal connection between the treatment module transmitter and the monitoring module receiver.

28. The device of claim 27, wherein the transmitter is an optical emitter or an RF transmitter.

29. The device of claim 21, wherein the treatment and monitoring modules are connected to a common control panel with inputs and outputs, each connected such that the monitoring module is operatively isolated from the treatment module so as to prevent the monitoring module from sending signals to the treatment module at all times.

30. The device of claim 21, wherein the monitoring module includes at least one display and at least one control configured to permit the selection of information to be shown on the display.

31. The device of claim 30, wherein the monitoring module is positioned adjacent to the treatment module such that a single user has simultaneous access to the at least one control of the treatment unit and the at least one display and at least one control of the monitoring module.

32. The device of claim 21, wherein the treatment module is a dialysis machine and the medical treatment is a dialysis treatment of blood from a patient.

33. The device of claim 21, wherein the treatment module is configured to operate as a stand-alone device without any input from said monitoring module.

34. The device of claim 21, wherein the treatment module includes at least one sensor for monitoring the administered medical treatment and the data signals sent to the monitoring module include a measurement by the at least one sensor.

35. The device of claim 21, wherein the treatment module includes at least one sensor configured to measure at least one of patient blood pressure, blood temperature, red blood cell count, volume of blood removed from the patient, and volume of fluid returned to the patient.

36. The device of claim 21, wherein the monitoring module is further configured to transfer treatment information to a remote device.

37. The device of claim 36, wherein the monitoring module is further configured to permit it to be controlled by the remote device.

* * * * *

UNITED STATES PATENT AND TRADEMARK OFFICE
CERTIFICATE OF CORRECTION

PATENT NO. : 7,771,379 B2  Page 1 of 1
APPLICATION NO. : 10/699921
DATED : August 10, 2010
INVENTOR(S) : Dennis M. Treu It is certified that error appears in the above-identified patent and that said Letters Patent is hereby corrected as shown below:

On the Title Page:

The Related U.S. Application Data should read as follows:

Related U.S. Application Data

(60)   This application is a continuation-in-part of Application No. 09/865,905 filed on May 24, 2001 (Patent No. 6,852,090), and claims the benefit of Provisional Application No. 60/423,318, filed on Nov. 1, 2002.

Signed and Sealed this

Twelfth Day of October, 2010

David J. Kappos
*Director of the United States Patent and Trademark Office*